(12) United States Patent
Masaki

(10) Patent No.: US 8,333,692 B2
(45) Date of Patent: Dec. 18, 2012

(54) ENDOSCOPE AND ENDOSCOPIC SYSTEM

(75) Inventor: Yutaka Masaki, Mitaka (JP)

(73) Assignee: Olympus Medical Systems Corp. (JP)

( * ) Notice: Subject to any disclaimer, the term of this patent is extended or adjusted under 35 U.S.C. 154(b) by 1220 days.

(21) Appl. No.: 12/139,872

(22) Filed: Jun. 16, 2008

(65) Prior Publication Data

US 2008/0249365 A1    Oct. 9, 2008

Related U.S. Application Data

(63) Continuation of application No. PCT/JP2006/320957, filed on Oct. 20, 2006.

(30) Foreign Application Priority Data

Dec. 26, 2005   (JP) .................................. 2005-373370

(51) Int. Cl.
A61B 1/00    (2006.01)

(52) U.S. Cl. .......................... 600/146; 600/152; 254/344

(58) Field of Classification Search .................. 254/344; 600/118, 139, 145, 146; 475/4, 5, 15, 204, 475/205, 251

See application file for complete search history.

(56) References Cited

U.S. PATENT DOCUMENTS

| 5,370,366 | A  | * | 12/1994 | Ottemann | 254/343 |
| 5,679,089 | A  | * | 10/1997 | Levedahl | 475/332 |
| 5,842,684 | A  | * | 12/1998 | Aho | 254/344 |
| 6,222,293 | B1 | * | 4/2001  | Ikeda et al. | 310/99 |
| 6,236,876 | B1 | * | 5/2001  | Gruner et al. | 600/407 |
| 6,554,766 | B2 | * | 4/2003  | Maeda et al. | 600/132 |
| 6,659,430 | B2 | * | 12/2003 | O'Fallon | 254/344 |
| 6,688,582 | B1 | * | 2/2004  | Wacinski | 254/297 |
| 6,932,761 | B2 | * | 8/2005  | Maeda et al. | 600/152 |
| 7,008,376 | B2 | * | 3/2006  | Ikeda et al. | 600/152 |
| 7,651,255 | B2 | * | 1/2010  | Ito | 362/574 |
| 2004/0049097 | A1 | * | 3/2004  | Miyake | 600/150 |
| 2004/0073083 | A1 | * | 4/2004  | Ikeda et al. | 600/101 |
| 2007/0232856 | A1 | * | 10/2007 | Ueno et al. | 600/118 |
| 2008/0262296 | A1 | * | 10/2008 | Suzuki | 600/106 |
| 2010/0268031 | A1 | * | 10/2010 | Koyama | 600/146 |

FOREIGN PATENT DOCUMENTS

JP   2000-279368   10/2000

(Continued)

OTHER PUBLICATIONS

International Search Report and Written Opinion mailed Jan. 16, 2007 in corresponding PCT International Application No. PCT/JP2006/320957.

English translation of International Preliminary Report dated Jul. 10, 2008 corresponding to International Patent Application No. PCT/JP2006/320957.

(Continued)

Primary Examiner — Matthew J Kasztejna
Assistant Examiner — Ryan Henderson
(74) Attorney, Agent, or Firm — Ostrolenk Faber LLP

(57) ABSTRACT

An endoscope includes an insertion portion having a bending portion, a base portion connected to the insertion portion, an operation wire extending from the bending portion toward the base portion, a drive source unit which is provided in the base portion, and a drive force transmission unit which is connected to the operation wire and the drive source unit. The drive source unit includes a first frame, a second frame, a motor, a gear box and a potentiometer. The gear box includes a horizontal power transmission mechanism for horizontally transmitting power from the motor, and an epicyclic gear mechanism for vertically transmitting power from the horizontal power transmission mechanism.

9 Claims, 9 Drawing Sheets

FOREIGN PATENT DOCUMENTS

| | | |
|---|---|---|
| JP | 2001-228410 | 8/2001 |
| JP | 2002-204776 | 7/2002 |
| JP | 2002-224016 | 8/2002 |
| JP | 2003-184903 | 7/2003 |
| JP | 2004-104931 | 4/2004 |
| JP | 2004-105747 | 4/2004 |
| JP | 2005-253614 | 9/2005 |
| JP | 2005-256936 | 9/2005 |
| JP | 2005-261688 | 9/2005 |

OTHER PUBLICATIONS

Office Action issued by the Japanese Patent Office on Feb. 14, 2012 in connection with corresponding Japanese Patent Application No. 2005-373370.

Translation of Office Action issued by the Japanese Patent Office on Feb. 14, 2012 in connection with corresponding Japanese Patent Application No. 2005-373370.

* cited by examiner

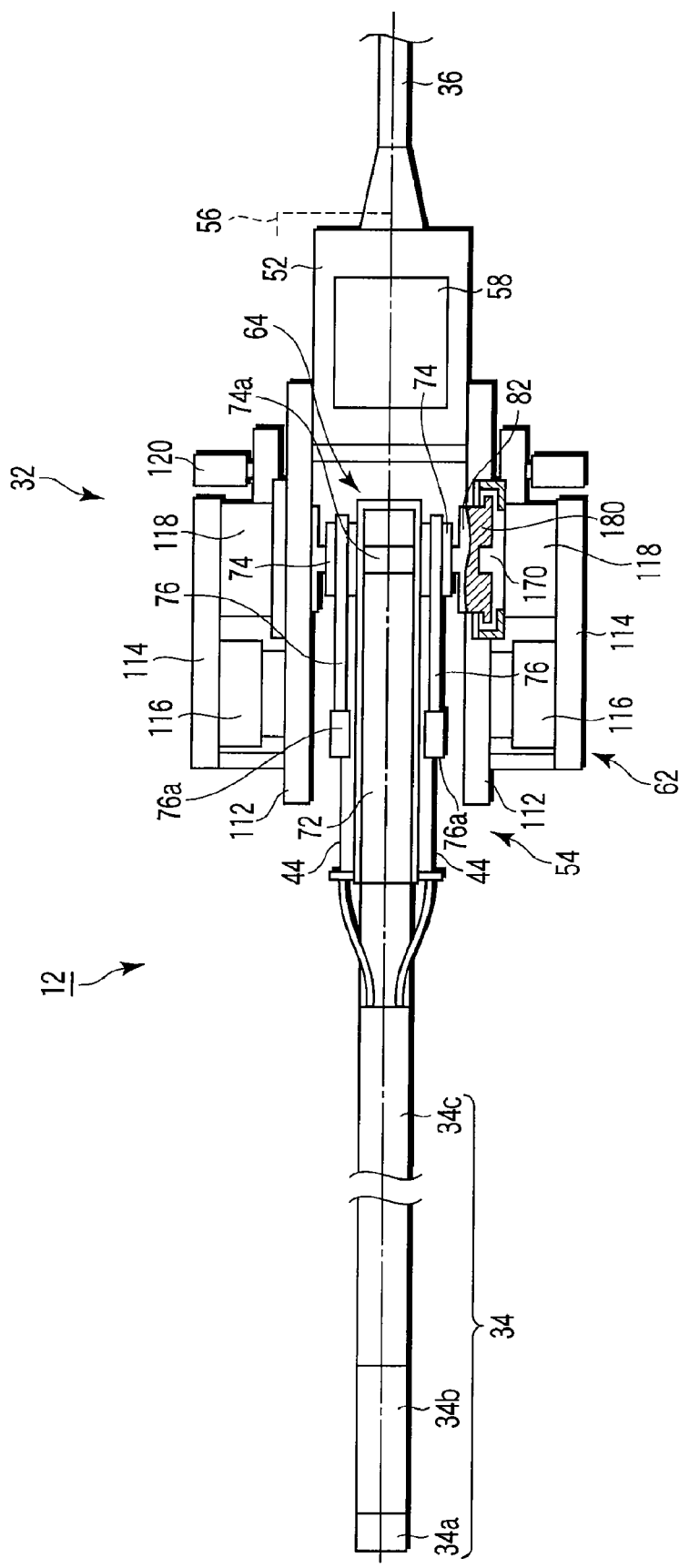
F I G. 2

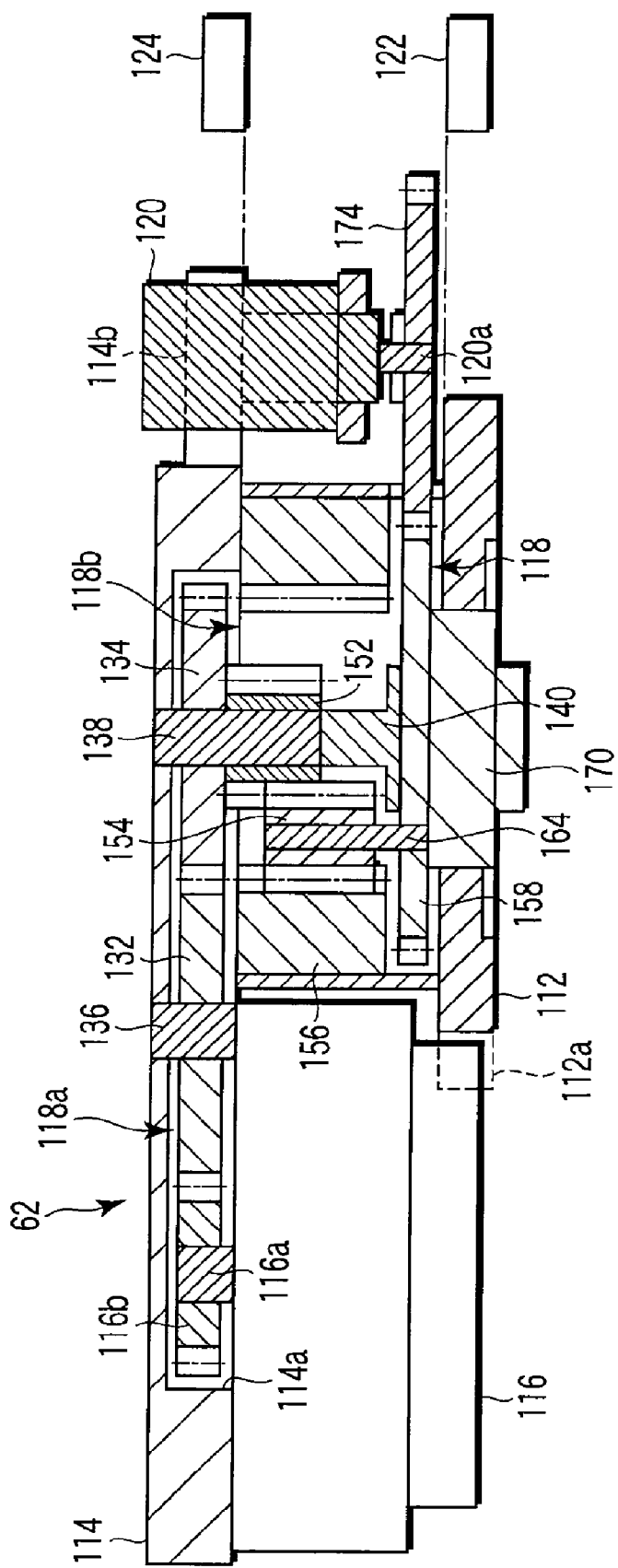
F I G. 4

ENDOSCOPE AND ENDOSCOPIC SYSTEM

CROSS REFERENCE TO RELATED APPLICATIONS

This is a Continuation Application of PCT Application No. PCT/JP2006/320957, filed Oct. 20, 2006, which was published under PCT Article 21(2) in Japanese.

This application is based upon and claims the benefit of priority from prior Japanese Patent Application No. 2005-373370, filed Dec. 26, 2005, the entire contents of which are incorporated herein by reference.

BACKGROUND OF THE INVENTION

1. Field of the Invention

The present invention relates to an endoscope and an endoscopic system capable of electrically bending a bending portion.

2. Description of the Related Art

Jpn. Pat. Appln. KOKAI Publication No. 2001-228410 has described an endoscope having an electrically bended bending portion which is formed by the combination of a reduction mechanism using gears and an endoscopic device.

As a reduction mechanism, an epicycle reduction gear described in Jpn. Pat. Appln. KOKAI Publication No. 2004-104931 is known. The epicycle reduction gear is suitable for the increase of a reduction ratio and the size reduction of a reduction mechanism.

BRIEF SUMMARY OF THE INVENTION

An endoscope according the invention includes: an insertion portion having a bending portion; a base portion provided on the proximal side of the insertion portion; an operation wire extending from the bending portion toward the base portion; a drive source unit which is provided in the base portion and which drives the operation wire; and a drive force transmission unit which is connected to the operation wire and the drive source unit and which transmits drive force driven by the drive source unit to the operation wire. Then, the drive source unit includes: a first plane which is disposed inside the base portion and which is parallel to the central axis of the insertion portion; a second plane which is provided in parallel to the first plane and which is provided at a position farther from the central axis of the insertion portion than the first plane; a drive source which is provided to project from the first plane toward the second plane in a state supported by the first plane and which generates drive force in the second plane; a first gear as a sun gear which is connected to permit the transmission of the drive force of the drive source and which is rotatably held on the second plane; a second gear as an epicyclic gear which is geared with the first gear and which rotates around the outer periphery of the first gear; a third gear which includes internal teeth geared with the second gear and which holds the second gear rotatably around the first gear; a fourth gear which is rotated on the first plane in accordance with the rotation of the second gear and which transmits the drive force from the drive source to the drive force transmission unit; and a rotational position detection mechanism which is provided to project from the first plane toward the second plane in a state supported by the second plane and which is connected to the fourth gear for the forward/backward movement of the operation wire to detect the rotational position of the fourth gear.

BRIEF DESCRIPTION OF THE SEVERAL VIEWS OF THE DRAWING

FIG. 2 is a schematic diagram showing the internal configuration of a base portion of an endoscope in the endoscopic system according to the first embodiment and an insertion portion;

FIG. 4 is a schematic sectional view showing the drive source unit of the base portion of the endoscope in the endoscopic system according to the first embodiment;

DETAILED DESCRIPTION OF THE INVENTION

A best mode for carrying out this invention will hereinafter be described with reference to the drawings.

A first embodiment is described with FIG. 1 to FIG. 4.

Figure 1:
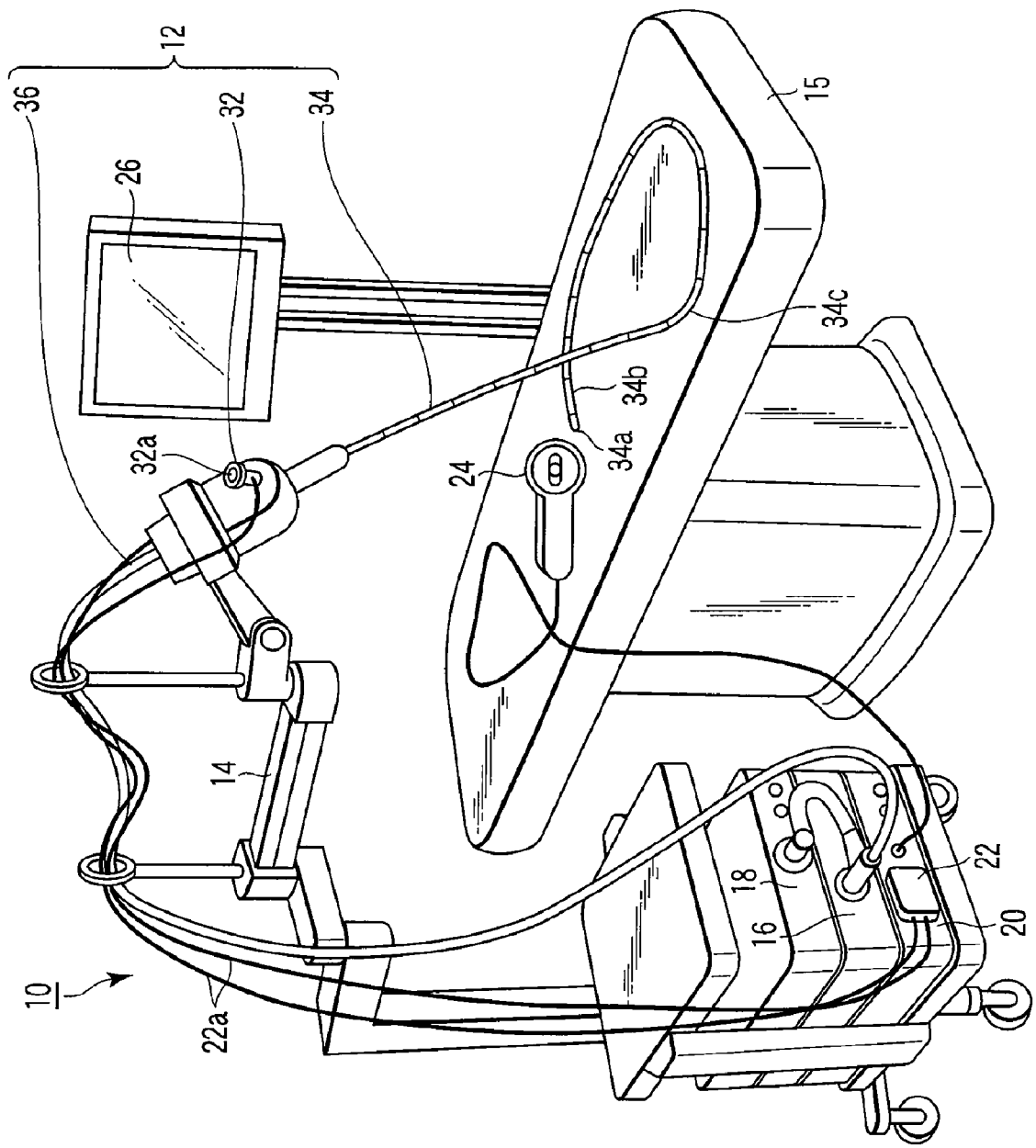
FIG. 1 is a schematic perspective view showing an endoscopic system according to a first embodiment of the present invention.

As shown in FIG. 1, an endoscopic system 10 according to this embodiment includes an electrically bending endoscope (medical instrument) 12, a supporter 14, a light source unit 16, a video processor 18, a pump unit 20, a fluid control cassette 22, an endoscopic remote controller 24 and a monitor 26.

The electrically bending endoscope 12 has functions to observe and treat the inside of a body cavity. The supporter 14 is properly disposed on the right or left of a bed 15. The supporter 14 arranges the light source unit 16, the video processor 18, the pump unit 20, etc., and supports the electrically bending endoscope 12 movably in a predetermined range. The light source unit 16 supplies an illumination light flux to be emitted from the front face of the distal end of an insertion portion 34 described later. The video processor 18 receives a video signal from an imaging unit (not shown) and subjects the video signal to predetermined signal processing. The pump unit 20 drives a flow volume adjusting mechanism of the fluid control cassette 22. In this pump unit 20, the driving of the flow volume adjusting mechanism is controlled by a signal of an air/water supply and suction operation input switch of the remote controller 24. The fluid control cassette 22 includes the flow volume adjusting mechanism having a valve element for air supply, water supply and suction, and is attachable to and detachable from the pump unit 20. The remote controller 24 includes an operation input device (e.g., a joystick) for electric bending, the air/water supply and suction operation input switch, and a scope switch (a remote switch for the freeze, release, etc. of the video processor).

The endoscope 12 includes a base portion 32 having, for example, a substantially cylindrical shape or a substantially columnar shape, the elongate insertion portion 34 extending from one side surface of the base portion 32, and an elongate universal cable 36 extending from the other side surface of the base portion 32. The insertion portion 34 and the universal cable 36 are coaxially disposed across the base portion 32. Both the insertion portion 34 and the universal cable 36 are flexible. The end of the universal cable 36 is optically connected to the light source unit 16, and electrically connected to the video processor 18. The above-mentioned remote controller 24 is an operation unit for bending a later-described bending portion 34b of the insertion portion 34 and for carrying out the air/water supply and suction. The remote controller 24 is electrically connected to, for example, an unshown system controller inside the pump unit 20.

The insertion portion 34 includes a distal hard portion 34a formed on the most distal side of the insertion portion 34, the bending portion 34b continuously provided on the proximal side of the distal hard portion 34a, and an elongate flexible tube portion 34c which is continuously provided on the proximal side of the bending portion 34b. The distal hard portion 34a has the built-in imaging unit (not shown) composed of an imaging optical system, an image pickup device such as a CCD, etc. The bending portion 34b is configured to vertically (UD) and horizontally (RL) bend by the driving control of a later-described bending drive mechanism 54 controlled in accordance with a bending operation instruction provided by the remote controller 24. The flexible tube portion 34c is subjected to force by the body wall in the body cavity and properly bent.

As shown in FIG. 2, angle wires (operation wires) 44 driven in response to the driving force from the bending drive mechanism 54 are inserted through the insertion portion 34. Two pairs of angle wires 44 are provided. The adjacent angle wires 44 are located 90 degrees away from each other with respect to the central axis of the insertion portion 34. These angle wires 44 are connected to the distal end of the bending portion 34b. Therefore, if the driving force from the bending drive mechanism 54 of the base portion 32 is transmitted to the angle wires 44, the bending portion 34b vertically and horizontally bends.

An air supply/water supply conduit and a suction conduit (both not shown) are inserted through the insertion portion 34. An air supply/water supply opening is made at the distal end of the air supply/water supply conduit, and a suction opening is made at the distal end of the suction conduit. The proximal end of the air supply/water supply conduit has an air supply/water supply opening at the base portion 32, and the proximal end of the suction conduit has a suction opening at the base portion 32. Tubes 22a (see FIG. 1) are connected on one end to the air supply/water supply opening at the proximal end of the air supply/water supply conduit and the suction opening at the proximal end of the suction conduit. That is, the tubes 22a are connected on one end to the base portion 32. In addition, the tubes 22a are connected on the other end to the fluid control cassette 22.

A forceps conduit (not shown) for inserting a surgical instrument such as forceps is inserted through the insertion portion 34. A forceps opening is made in the distal front surface of the forceps conduit. The proximal end of the forceps conduit is, at the proximal end of the insertion portion 34, in communication with a forceps insertion opening 32a (see FIG. 1) formed in the vicinity of the base portion 32. Thus, the surgical instrument such as the forceps inserted from the forceps insertion opening 32a can project from the distal front surface of the insertion portion 34 through the forceps conduit.

As shown in FIG. 2, the base portion 32 of the endoscope 12 includes a cylindrical frame 52, the bending drive mechanism 54 provided in the cylindrical frame 52, a cylindrical cover (cylindrical member) 56 as an outer envelope covering the cylindrical frame 52 and the bending drive mechanism 54, and a drive circuit 58 for controlling the bending drive mechanism 54. The endoscope 12 is supported on the supporter 14 by the cylindrical cover 56 of the base portion 32.

Figure 3A:
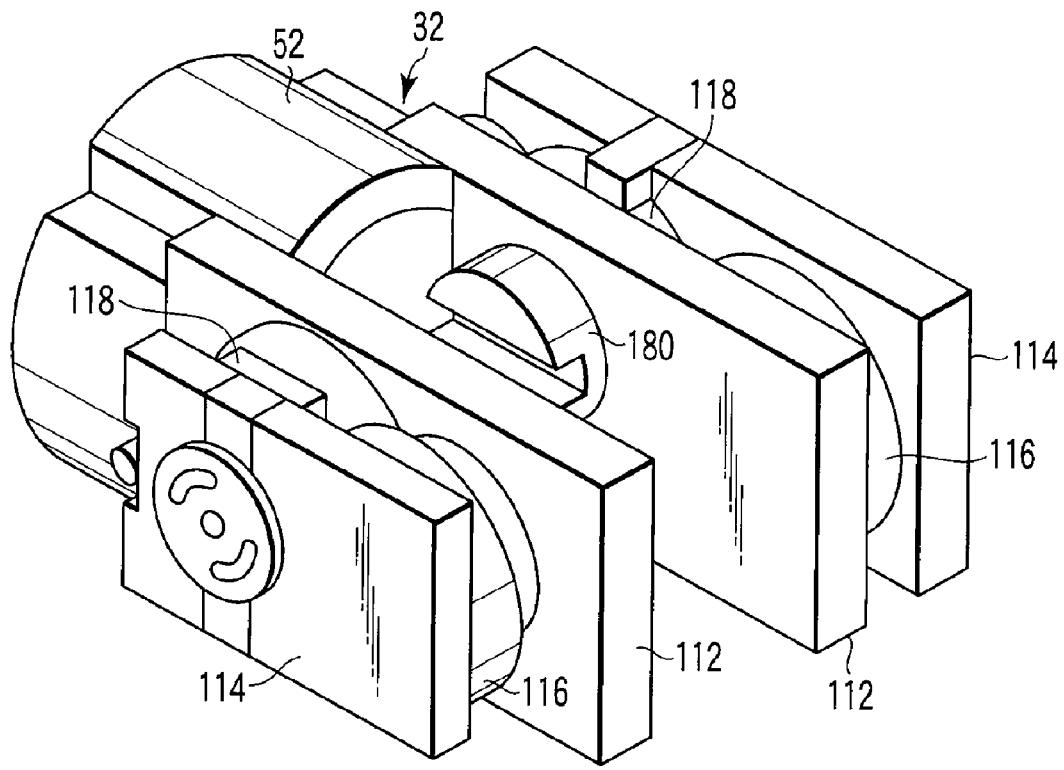
FIG. 3A is a schematic perspective view showing a cylindrical frame and a drive source unit of the base portion of the endoscope in the endoscopic system according to the first embodiment.

The bending drive mechanism 54 includes a pair of drive source units (motor units) 62, and a drive force transmission unit 64 for transmitting drive force driven by the drive source units 62 to the angle wires 44. The drive source units 62 are disposed in a state fixed to the cylindrical frame 52. As shown in FIG. 2 and FIG. 3A, the drive force transmission unit 64 is attachable to and detachable from the cylindrical frame 52.

As shown in FIG. 2, the drive force transmission unit 64 includes a drive force transmission unit frame 72 for forming the drive force transmission unit 64, a pair of sprockets 74, and a pair of chains 76. Of the pair of sprockets 74 and the pair of chains 76, one sprocket 74 and one chain 76 are provided to vertically bend the bending portion 34b, while the other sprocket 74 and the other chain 76 are provided to horizontally bend the bending portion 34b.

A pair of shafts 74a rotatably supported by unshown bearing is disposed in the drive force transmission unit frame 72. The sprockets 74 are fixed to the ends of the shafts 74a, respectively. These shafts 74a are coaxially arranged. That is, a pair of sprockets 74 is rotatably attached to the frame 72 by the shafts 74a, respectively.

The chain 76 is wound around each of the pair of sprockets 74 shown in FIG. 2. Both ends of the chains 76 are oriented toward the distal end of the insertion portion 34. The proximal ends of the angle wires 44 are detachably connected to both ends of the chains 76 by connecting members 76a, respectively. The distal ends of the angle wires 44 are connected to the distal end of the bending portion 34b having a joint ring (not shown), respectively. Especially, the distal ends of one pair of angle wires 44 are fixed at positions opposite to each other with respect to the central axis of the joint ring of the bending portion 34b. The distal ends of the other pair of angle wires 44 are fixed at positions opposite to each other with respect to the central axis of the joint ring of the bending portion 34b and 90 degrees away from the adjacent wires 44 with respect to the central axis of the joint ring. Moreover, the two pairs of angle wires 44 are guided in proximity to the drive force transmission unit 64 to the above-mentioned positions, and extended and fixed to the distal end of the bending portion 34b of the insertion portion 34.

On one side of each of the sprockets 74 shown in FIG. 2, a joint 82 (see FIG. 3A to FIG. 3C) for detachably connected to the drive source units 62 is integrally formed, or turned to the end in a fitted state and fixed. One side of the sprocket 74 referred to here is a side away from the central axis of the insertion portion 34 (the central axis of the drive force transmission unit 64).

Figure 3B:
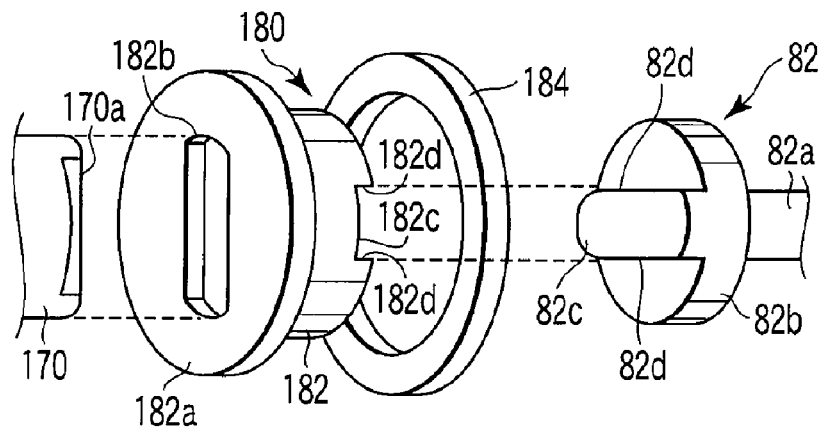
FIG. 3B is a schematic perspective view showing an Oldham's coupling disposed in an output shaft of the drive source unit of the base portion of the endoscope in the endoscopic system according to the first embodiment, and also showing a joint of a drive force transmission unit which is fitted into the Oldham's coupling.

As shown in FIG. 3B, the joint 82 includes a disk 82b disposed on a shaft 82a extending from one side of the sprocket 74, and a projection 82c provided on the surface of the disk 82b. The shaft 82a of the joint 82 is disposed coaxially with the above-mentioned shafts 74a. The projection 82c passes the central axis of the disk 82b, and is diametrically formed up to the edge of the disk 82b. Further, a pair of slide surfaces 82d is formed in the projection 82c. These slide surfaces 82d are fitted by sliding into slide surfaces 182d of a recess 182c of a later-described floating cam 182 of a later-described Oldham's coupling 180. That is, the joint 82 is detachably fitted into the Oldham's coupling 180. Thus, output from an output shaft 170 is transmitted to the joint 82 via the Oldham's coupling 180, and can be transmitted to, for example, the sprockets 74 for vertical bending and horizontal bending.

In addition, the disk 82b of the joint 82 is provided with the projection 82c in the above description, but the projection 82c may be provided in one of the two joints 82, and a recess (not shown) may be provided in the disk 82b of the other joint 82. Thus, the direction in which the drive force transmission unit 64 is arranged by the sliding of the slide surfaces 82d, 182d is uniquely determined. That is, it is possible to readily recognize the direction of the drive force transmission unit 64 with respect to the drive source unit 62.

As shown in FIG. 2, one pair of drive source units 62 is provided in the cylindrical frame 52 symmetrically with respect to the central axis of the insertion portion 34 coaxial with the central axis of the cylindrical frame 52, in order to bend the bending portion 34b separately in the vertical direction and in the horizontal direction. The pair of drive source units 62 is symmetrically configured in configuration and arrangement. Therefore, the drive source units 62 are symmetrically balanced in weight with respect to the central axis of the insertion portion 34, resulting in reduced disproportion. Thus, when the insertion portion 34 is turned (the insertion portion 34 is twisted) while the base portion 32 of the endoscope 12 is being supported by the supporter 14, uneven torque of the rotation can be reduced. Therefore, the configuration of one drive source unit 62 is representatively explained.

As shown in FIG. 4, the drive source unit 62 includes a first frame 112, a second frame 114, a motor (drive source) 116, a gear box 118 and a potentiometer (rotational position detection mechanism) 120. The surfaces (a first plane 122 and a second plane 124 in FIG. 4) of the first frame 112 and the second frame 114 are arranged in parallel with each other.

The motor 116 is flatly formed, and is reduced in diameter at its proximal end opposite to its distal end where a drive shaft 116a projects. That is, a step, for example, is formed at the proximal end of the motor 116. On the other hand, a cutout 112a is formed in the first frame 112. The proximal end of the motor 116 is disposed in and fixed to the cutout 112a of the first frame 112. In particular, the proximal end of the motor 116 is disposed in close contact with the cutout 112a of the first frame 112. Here, the first frame 112 is formed of a member having a high thermal conductivity such as a metal material. Therefore, the motor 116 can be disposed in a small range, and heat generated by the driving of the motor 116 can be transmitted to the first frame 112. Thus, the first frame 112 functions as a heat sink of the motor 116.

On the other hand, the drive shaft 116a at the distal end of the motor 116 is disposed in a recess 114a of the second frame 114. A motor pinion 116b is fixed to the drive shaft 116a of the motor 116. Thus, the motor pinion 116b rotates together with the rotation of the drive shaft 116a of the motor 116.

Here, the gear box 118 includes a horizontal power transmission mechanism 118a for horizontally transmitting power by the motor pinion 116b, and an epicyclic gear mechanism 118b for vertically transmitting power from the horizontal power transmission mechanism 118a.

The horizontal power transmission mechanism 118a includes a first spur gear 132 and a second spur gear 134. The first spur gear 132 can rotate around the central axis (pivot) of a first spur gear shaft 136 supported in a state fixed to the recess 114a of the second frame 114. The second spur gear 134 can rotate around the central axis (pivot) of a second spur gear shaft (hereinafter referred to as a sun gear shaft) 138 supported in a state fixed to the recess 114a of the second frame 114. In particular, the sun gear shaft 138 is fixed to and supported on the second frame 114 in a cantilevered manner. The sun gear shaft 138 extends straight toward the first frame 112. A thrust bearing 140 is disposed between the sun gear shaft 138 and a fourth gear 158 described later.

Furthermore, the first spur gear 132 is geared with the motor pinion 116b. The second spur gear 134 is geared with the first spur gear 132. Thus, power is transmitted to the second spur gear 134 from the motor pinion 116b via the first spur gear 132 by the rotation of the drive shaft 116a of the motor 116. In addition, the first spur gear 132 and the second spur gear 134 are disposed in the recess 114a of the second frame 114 in the same manner as the motor pinion 116b.

The epicyclic gear mechanism 118b is disposed in the second spur gear 134 toward the first frame 112. The epicyclic gear mechanism 118b includes first to fourth gears 152, 154, 156 and 158. The first gear 152 is a sun gear. The first gear 152 is formed integrally with the above-mentioned second spur gear 134. The first gear 152 has a hollow structure as the sun gear shaft 138 penetrates therethrough, and is rotatably fitted to the sun gear shaft 138. Therefore, the second spur gear 134 and the first gear (sun gear) 152 are rotatable around the fixed sun gear shaft 138. Here, both or at least one of the first gear 152 and the sun gear shaft 138 are surface-hardened to improve abrasion resistant properties.

The second gear 154 is geared with the first gear 152. The third gear 156 is geared with the second gear 154. The third gear 156 is formed into a ring shape or a cylindrical shape, and is fixed to the gear box 118. The third gear 156 is disposed concentrically with the first gear 152. The second gear 154 can rotate around the first gear 152. Thus, the second gear 154 moves along the inner periphery of the third gear 156. That is, the second gear 154 rotates on its axis and at the same time revolves around the first gear 152.

Furthermore, an epicyclic gear shaft (second gear shaft) 164 is disposed on the central axis of the second gear 154. The epicyclic gear shaft 164 extends toward the first frame 112. The fourth gear 158 is supported on an extended end of the epicyclic gear shaft 164. The fourth gear 158 is formed into a disk shape having the same central axis as the sun gear shaft 138. Thus, the second gear 154 rotates on its axis and at the same time revolves around the first gear 152 such that the fourth gear 158 rotates around the sun gear shaft 138.

The output shaft 170 is fixed to the fourth gear 158. The output shaft 170 penetrates the first frame 112, and is rotatably supported by an unshown bearing. That is, the output shaft 170 projects from the first frame 112 toward the central axis of the insertion portion 34 (the central axis of the drive force transmission unit 64). Here, both or at least one of the output shaft 170 and the first frame 112 are surface-hardened to improve abrasion resistant properties.

A cutout 114b is formed at the end of the second frame 114. In the cutout 114b, the potentiometer 120 for detecting the rotational position of the output shaft 170 (the fourth gear 158) is disposed. The potentiometer 120 is disposed from the first frame 112 toward the second frame 114. In particular, the proximal end of the potentiometer 120 is disposed in close contact with the cutout 114b of the second frame 114. Here, the second frame 114 is formed of a member having a high thermal conductivity such as a metal material. Therefore, the potentiometer 120 can be disposed in a small range, and heat generated by the rotation of a rotation shaft 120a of the potentiometer 120 can be transmitted to the second frame 114. Thus, the second frame 114 functions as a heat sink of the potentiometer 120.

The potentiometer 120 is disposed at a position adjacent to the epicyclic gear mechanism 118b and away from the motor 116. That is, the epicyclic gear mechanism 118b is disposed between the potentiometer 120 and the motor 116.

A meter gear 174 is fixed to the rotation shaft 120a of the potentiometer 120. The meter gear 174 is geared with the fourth gear 158 inside the gear box 118. Here, the number of teeth of the meter gear 174 is the same as the number of teeth of the fourth gear 158. Therefore, the position of the fourth gear 158 (the output shaft 170) is transmitted to the potentiometer 120 via the meter gear 174 and detected by the potentiometer 120. Thus, the potentiometer 120 can be disposed in a small range at a position proximate to the fourth gear 158. In addition, the meter gear 174 may be made of a metal material, but is preferably made of a plastic material.

Although not shown, the motor 116, the potentiometer 120, etc., are electrically connected to the above-mentioned drive circuit 58. The drive circuit 58 is electrically connected to the remote controller 24. Therefore, the motor 116 is controlled by output from the drive circuit 58 which receives a signal based on the operation of the remote controller 24. Then, a signal detected by the potentiometer 120 is input to the drive circuit 58. In this manner, the rotation amount of the motor 116 is feedback-controlled. In addition, the use of the potentiometer 120 to detect the rotation amount is described in this embodiment, but it is also preferred to use, for example, an encoder or resolver instead of the potentiometer 120.

As described above, the output shaft 170 is disposed in the fourth gear 158. A fit portion 170a of the output shaft 170 shown in FIG. 3B is formed to project in an elliptical shape. The Oldham's coupling 180 is disposed in the output shaft 170. The Oldham's coupling 180 includes the floating cam 182 and a floating cam holding ring 184. The Oldham's coupling 180 is disposed between the output shaft 170 and the above-mentioned first frame (drive force transmission unit guide frame) 112.

Figure 3C:
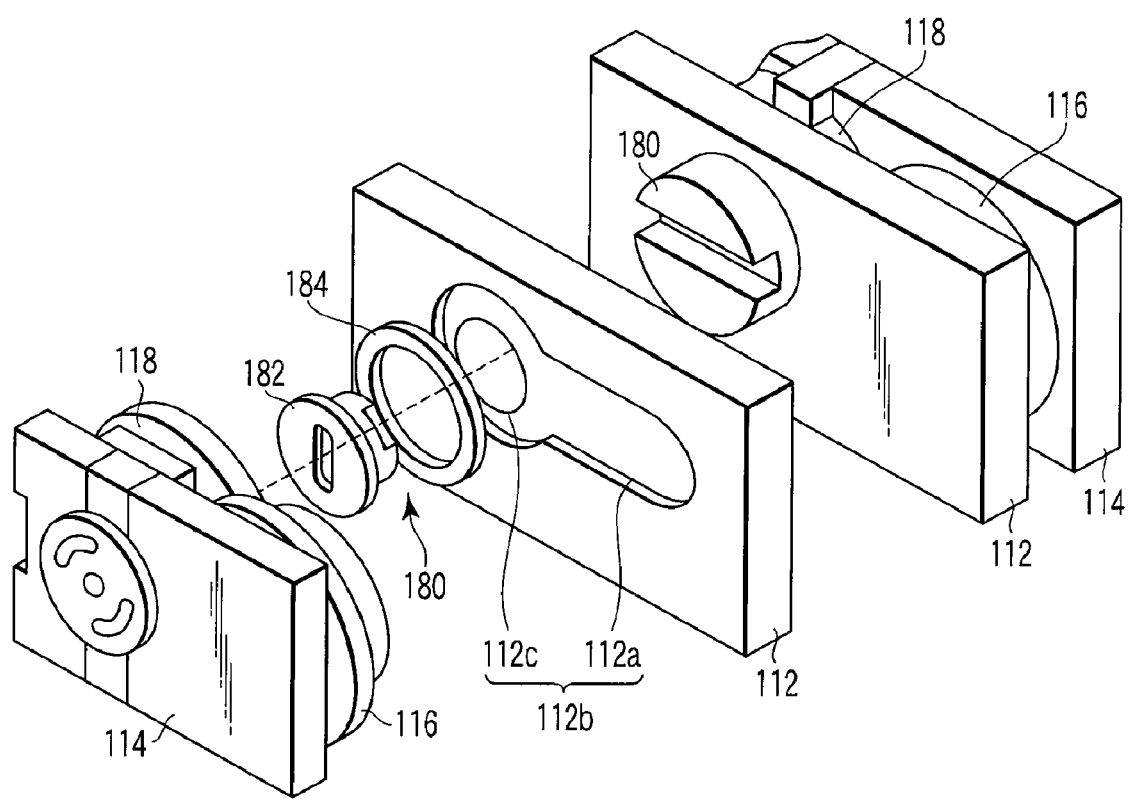
FIG. 3C is a schematic partial exploded perspective view showing the drive source unit of the base portion of the endoscope in the endoscopic system according to the first embodiment.

A frame recess 112b is formed in the first frame 112. The frame recess 112b includes the above-mentioned cutout (motor disposal portion) 112a in which the motor 116 is disposed, and a through-hole 112c in which the floating cam 182 penetrating the first frame 112 is disposed. In addition, although the cutout 112a is shown in a penetrating state in FIG. 4, the cutout 112a may be in a non-penetrating state as shown in FIG. 3C.

The floating cam 182 is formed into a columnar shape having a diametrically outwardly projecting flange portion 182a at one end. An elliptic (substantially oval) output shaft fit recess 182b is formed in the center of one end face at one end of the floating cam 182. The likewise elliptic fit portion 170a of the output shaft 170 is fitted into the recess 182b. On the other hand, at the other end of the floating cam 182, the recess 182c is formed in a direction perpendicular to the longitudinal direction of the recess 182b formed at one end. In the recess 182c at the other end face, the slide surfaces 182d are formed into which the projection 82c of the joint 82 formed integrally with the sprocket 74 of the drive force transmission unit 64 is slidably fitted. In addition, the joint 82 can be attached/detached by horizontally disposing the recess 182c at the other end of the floating cam 182, and sliding the slide surfaces 82d of the projection 82c of the joint 82 over the slide surfaces 182d of the recess 182c of the floating cam 182 when the projection 82c of the joint 82 is horizontally disposed. Thus, maintenance can be easily done on the drive source unit 62 and the drive force transmission unit 64.

The holding ring 184 has an inside diameter smaller than the diameter of the flange portion 182a of the floating cam 182 and larger than the diameter of the columnar portion of the floating cam 182. Further, this holding ring 184 is disposed around the through-hole 112c of the frame recess 112b. The floating cam 182 is disposed so that the flange portion 182a is in contact with the holding ring 184 in order for the holding ring 184 to be in contact with the frame recess 112b. Moreover, the fit portion 170a of the output shaft 170 is fitted into the recess 182b on one end face of the floating cam 182. As the flange portion 182a of the floating cam 182 is pressed by the holding ring 184, the output shaft 170 and the floating cam 182 are prevented from being detached from each other.

Next, the effects of the endoscope 12 according to this embodiment will be described.

The operation unit of the remote controller 24 shown in FIG. 1 is operated. That is, the remote controller 24 is operated to bend the bending portion 34b of the endoscope 12. A signal output from the remote controller 24 is input to the drive circuit 58 of the base portion 32 through the system controller and the universal cable.

The drive circuit 58 rotates the drive shaft 116a of the motor 116 in a desired direction in accordance with the operation of the remote controller 24. Owing to the rotation of the drive shaft 116a of the motor 116, the second spur gear 134 rotates via the motor pinion 116b and the first spur gear 132. Thus, drive force is transmitted to the first gear 152 integral with the first gear (sun gear) 152 from the drive shaft 116a of the motor 116. Then, the first gear 152 rotates owing to the rotation of the second spur gear 134. Owing to the rotation of the first gear 152, the second gear (epicyclic gear) 154 geared with the first gear 152 rotates. At this point, as the third gear 156 is fixed to the gear box 118, the second gear 154 rotates on its axis and at the same time revolves around the first gear 152. That is, the second gear 154 moves along the inside (internal teeth) of the third gear 156 while rotating on its axis.

At this point, the fourth gear 158 is rotated in accordance with the revolution of the second gear 154. That is, the fourth gear 158 rotates around the central axis (the sun gear shaft 138) of the first gear 152 by the epicyclic gear shaft 164 on the central axis of the second gear 154 which revolves around the first gear 152. Thus, turning force is output from the output shaft 170 fixed to the fourth gear 158.

Therefore, the drive force of the drive shaft 116a of the motor 116 on the side of the second frame 114 is transferred to the output shaft 170 on the side of the first frame 112 such that the turning force is transmitted. At this moment, the turning force is output from the output shaft 170 so that the rotation of the drive shaft 116a of the motor 116 is reduced to a great extent.

The fourth gear 158 outputs the turning force from the output shaft 170, and at the same time rotates the rotation shaft 120a of the potentiometer 120 via the meter gear 174 geared with the fourth gear 158. The potentiometer 120 detects the rotation number of the meter gear 174 having the same number of teeth as that of the fourth gear 158, and outputs the rotation number to the drive circuit 58. The drive circuit 58 judges the rotation amount of the meter gear 174 on the basis of the rotation number. That is, the drive circuit 58 judges the rotation amount of the fourth gear 158.

The Oldham's coupling 180 is disposed in the output shaft 170. Thus, the turning force of the output shaft 170 is transmitted to the floating cam 182. The projection 82c of the joint 82 of the drive force transmission unit 64 is fitted into the recess 182c of the floating cam 182 by sliding. Thus, the turning force is transmitted from the output shaft 170 to the joint 82 via the floating cam 182 such that the sprocket 74 rotates around the shaft 74a. Owing to the rotation of the sprocket 74, the chains 76 move in the axial direction of the insertion portion 34. Therefore, the angle wires 44 move along the axial direction of the insertion portion 34. Then, the bending portion 34b bends in a desired direction. Thus, the above-mentioned signal detected by the potentiometer 120 judges the bending state of the bending portion 34b.

As described above, the following effects can be obtained according to this embodiment.

The drive force of the drive shaft 116a of the motor 116 on the side of the second frame 114 is transferred to the opposite output shaft 170 on the side of the first frame 112 through the horizontal power transmission mechanism 118a and the epicyclic gear mechanism 118b such that the turning force is transmitted. Thus, the thickness of the drive source unit 62 can be smaller than when the drive force is transmitted on the same axis. Moreover, the use of the epicyclic gear mechanism 118b makes it possible to provide a slower output from the output shaft 170 than that of the drive shaft 116a of the motor 116 in a desired reduction ratio.

Furthermore, as the cutouts 112a, 114b are provided in the first frame 112 and the second frame 114, the motor 116 and the potentiometer 120 can be arranged with a smaller thickness of the drive source unit 62.

That is, the use of the epicyclic gear mechanism (reduction mechanism) 118b makes it possible to reduce the part of the reduction mechanism 118b in size. Further, the motors (drive sources) 116 connected to the sun gear 152 which is the first stage of the epicyclic gear mechanism 118b, and the potentiometers (rotational position detection mechanisms) connected to the fourth gear 158 which is the final stage are projectingly provided opposite to each other. Thus, the whole mechanism can be formed to have a small thickness and installed inside the base portion 32. As a result, the base portion 32 of the endoscope 12 can be reduced in size. That is, the size of the endoscope 12 can be reduced.

Furthermore, the Oldham's coupling 180 enables the output shaft 170 of the drive source unit 62 and the joint 82 of the drive force transmission unit 64 to be attached to and detached from each other by sliding. Thus, the maintenance of the drive source unit 62 and the drive force transmission unit 64 can be easily done.

Next, a second embodiment will be described with FIG. 5 to FIG. 9. This embodiment is a modification of the first embodiment, and the same sings are assigned to the same members as those described in the first embodiment or members having the same function, and such members are not described in detail.

This embodiment shows an example in which a differential epicyclic gear mechanism 118c (see FIG. 5 and FIG. 6) different from the epicyclic gear mechanism 118b described in the first embodiment is used, and this embodiment also describes an example in which there is provided a clutch mechanism 270 (FIG. 6 to FIG. 9) switchable between a state (first state) where the drive force of a motor 116 is transmitted to an output shaft 170 and a state (second state) where the transmission of the drive force is cancelled.

Figure 5:
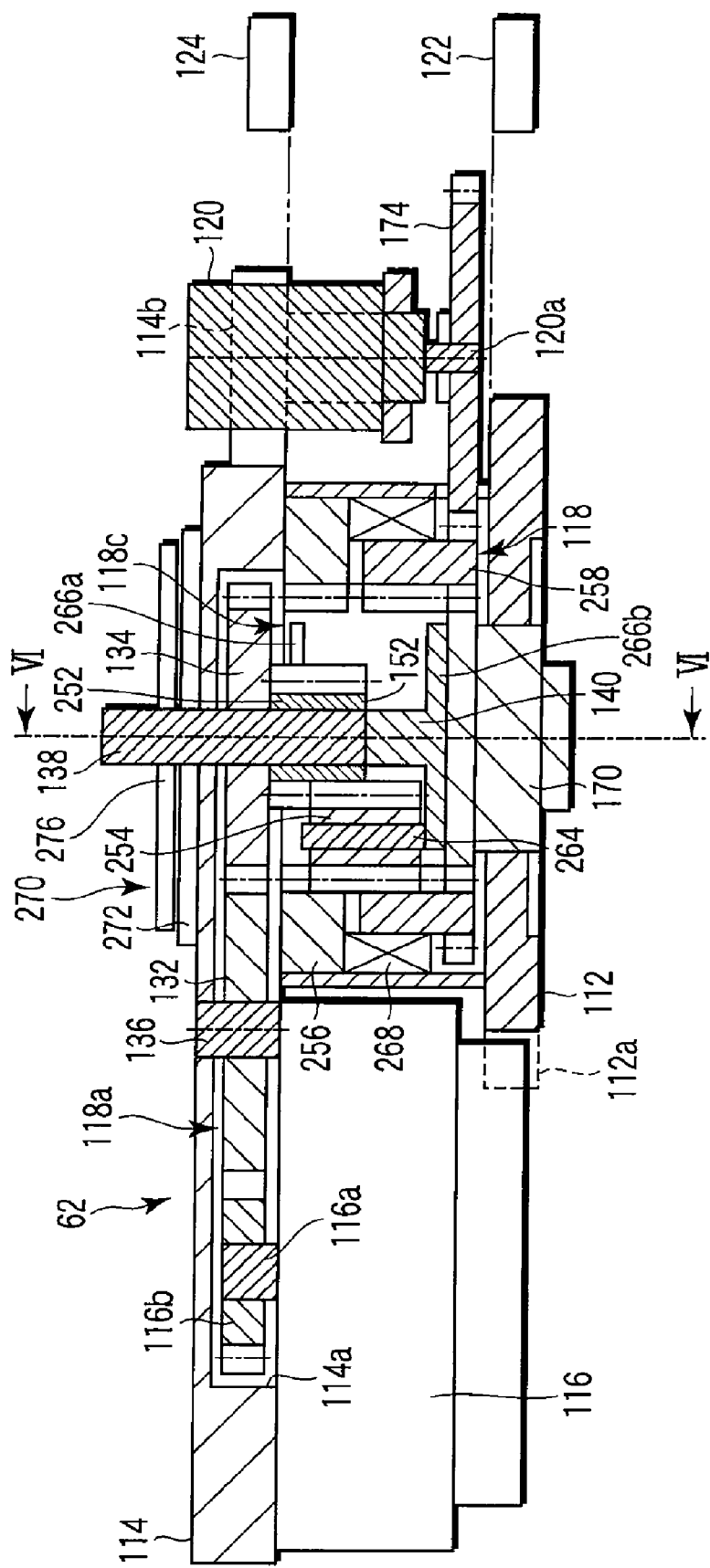
FIG. 5 is a schematic sectional view along the V-V line in FIG. 6, showing a drive source unit of a base portion of an endoscope in an endoscopic system according to a second embodiment of the present invention.

As shown in FIG. 5, a drive source unit 62 includes a gear box 118, as in the first embodiment. In addition to the above-mentioned horizontal power transmission mechanism 118a, the gear box 118 includes the differential epicyclic gear mechanism 118c which vertically transmits power from the horizontal power transmission mechanism 118a. That is, this embodiment is an example in which the differential epicyclic gear mechanism 118c is used instead of the epicyclic gear mechanism 118b described in the first embodiment.

The differential epicyclic gear mechanism 118c is disposed in a second spur gear 134 toward a first frame 112 as the epicyclic gear mechanism 118b is disposed in the second spur gear 134 toward the first frame 112 in the first embodiment. The differential epicyclic gear mechanism 118c includes first to fourth gears 252, 254, 256 and 258. The first gear 252 is a sun gear. The first gear 252 is formed integrally with the above-mentioned second spur gear 134. The first gear 252 has a hollow structure as a sun gear shaft 138 penetrates therethrough, and the first gear 252 is rotatably fitted into the sun gear shaft 138. Therefore, the second spur gear 134 and the first gear (sun gear) 252 are rotatable around the fixed sun gear shaft 138. Here, both or at least one of the first gear 252 and the sun gear shaft 138 are surface-hardened to improve abrasion resistant properties.

The second gear 254 which is an epicyclic gear is geared with the first gear 252. An epicyclic gear shaft (second gear shaft) 264 is disposed on the central axis of the second gear 254. The epicyclic gear shaft 264 is disposed between a first carrier 266a and a second carrier 266b. That is, the second gear 254 is constrained in the axial direction, but is free in the radial direction perpendicular to the axial direction. Thus, the second gear 254 rotates and self-aligns at the same time during rotation on its axis or revolution around. Then, the machining error or assembly error of the second gear 254 is properly eliminated.

The internal teeth of the third gear 256 which is a profile shifted gear are geared with the second gear 254. The third gear 256 is formed into a ring shape or a cylindrical shape. The third gear 256 can be switched by the clutch mechanism 270 to the first state (fixed state) or the second state (rotatable state). The third gear 256 is disposed concentrically with the first gear 252. The second gear 254 is rotatable around the first gear 252. Thus, when the third gear 256 is in the first state, the second gear 254 moves along the inner periphery of the third gear 256. That is, the second gear 254 rotates on its axis and at the same time revolves around the first gear 252.

The internal teeth of the fourth gear 258 which is a profile shifted gear are additionally geared with the second gear 254. The fourth gear 258 is formed into a ring shape or a cylindrical shape. The fourth gear 258 is disposed concentrically with the first gear 252. Further, part of the outer periphery of the fourth gear 258 is supported by a bearing 268 disposed on the inner peripheral surface of the gear box 118. That is, the fourth gear 258 rotates around the same central axis as the sun gear shaft 138.

Here, the third gear 256 and the fourth gear 258 are both geared with the second gear 254, but have a difference in the number of teeth, for example, by several teeth. The number of teeth of the third gear 256 is smaller than that of the fourth gear 258. As the fourth gear 258 is geared with the second gear 254 in the same manner as the third gear 256, the fourth gear 258 rotates by receiving force so that the difference in the number of teeth between the fixed third gear 256 and the fourth gear 258 may be reduced. Thus, a reduced output (torque) is provided from the fourth gear 258 to a drive shaft 116a of the motor 116. Therefore, the use of the differential epicyclic gear mechanism 118c allows a high reduction ratio.

External teeth are formed at the proximal end of the output shaft 170 disposed between the first frame 112 and the second frame 114. These external teeth are spline-fitted into the internal teeth of the fourth gear 258. The number of the internal teeth of the fourth gear 258 is the same as the number of the external teeth of the output shaft 170. Further, the thickness of the external teeth of the output shaft 170 is formed slightly smaller than the thickness of the internal teeth of the fourth gear 258. Thus, torque can be applied by all of the internal teeth of the fourth gear 258 and the external teeth of the output shaft 170. Therefore, the internal teeth of the fourth gear 258 and the external teeth of the output shaft 170 can be reduced in thickness and can both be formed into small sizes. Owing to a clearance of the spline-fit in such a configuration, even the slight eccentricity of the internal teeth of the fourth gear 258 and the external teeth of the output shaft 170 can be permitted if any. In addition, the sun gear shaft 138 which is a fixed shaft and the first frame 112 can be used as receivers in the thrust direction of the output shaft 170.

The output shaft 170 is rotatably supported on the first frame 112. The output shaft 170 projects from the first frame 112 toward the central axis of an insertion portion 34 (the central axis of a drive force transmission unit 64). Further, an Oldham's coupling 180 is disposed in a fit portion 170a of the output shaft 170.

A meter gear 174 of a potentiometer 120 is geared with the external teeth of the fourth gear 258 inside the gear box 118. Here, the number of teeth of the meter gear 174 is the same as the number of teeth of the fourth gear 258. Thus, the rotation amount (position) of the fourth gear 258 (the output shaft 170) is transmitted to the potentiometer 120 via the meter gear 174 and detected by the potentiometer 120.

Figure 6:
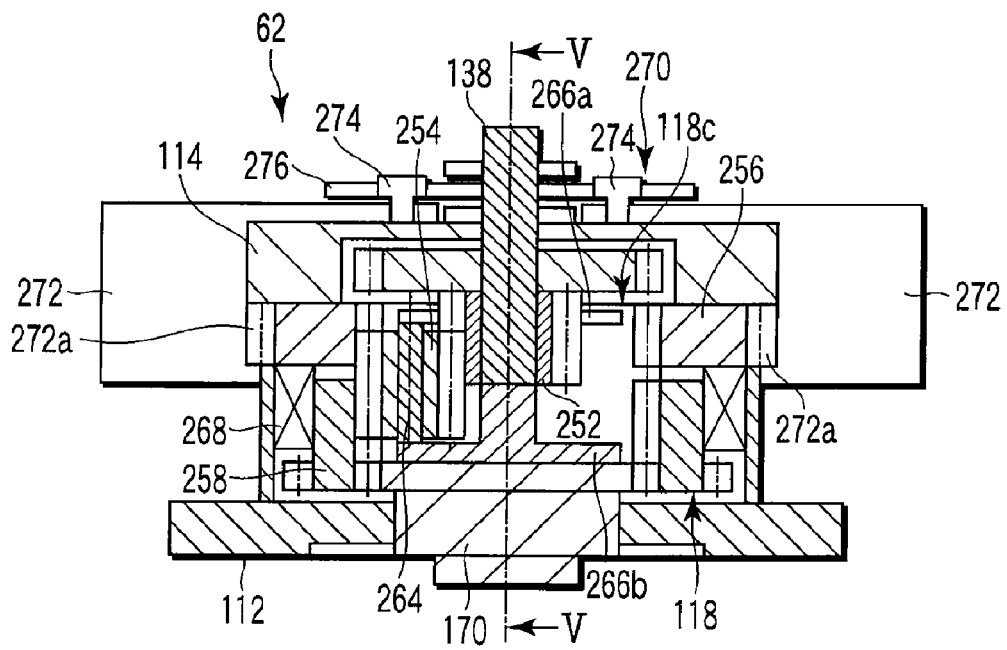
FIG. 6 is a schematic sectional view along the VI-VI line in FIG. 5, showing the drive source unit of the base portion of the endoscope in the endoscopic system according to the second embodiment.
Figure 7A:
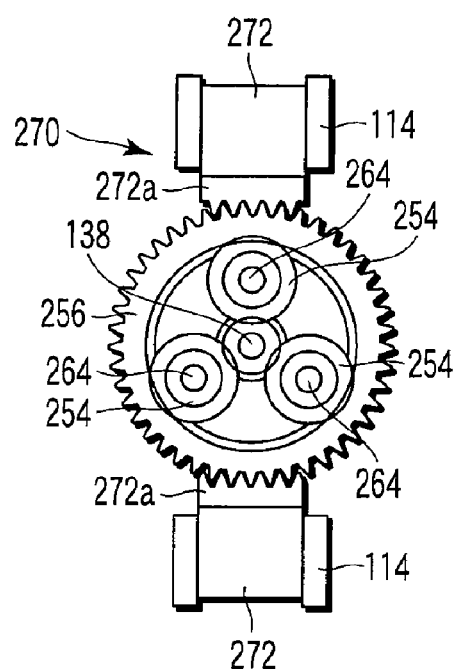
FIG. 7A is a schematic diagram showing the outline of a clutch mechanism disposed in the drive source unit of the base portion of the endoscope in the endoscopic system according to the second embodiment, and showing a case where drive force is transmitted from a motor as a drive source.
Figure 7B:
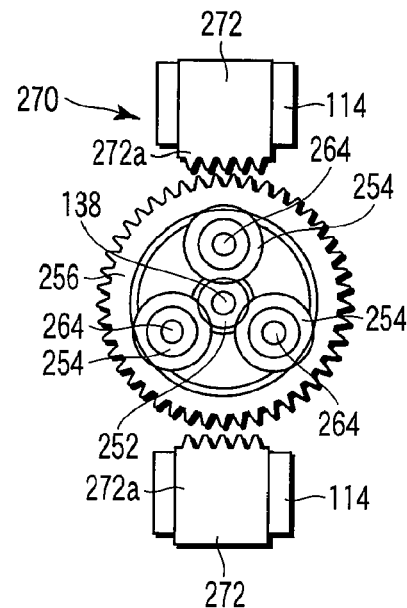
FIG. 7B is a schematic diagram showing the outline of the clutch mechanism disposed in the drive source unit of the base portion of the endoscope in the endoscopic system according to the second embodiment, and showing a case where the drive force is not transmitted from the motor as the drive source.
Figure 8:
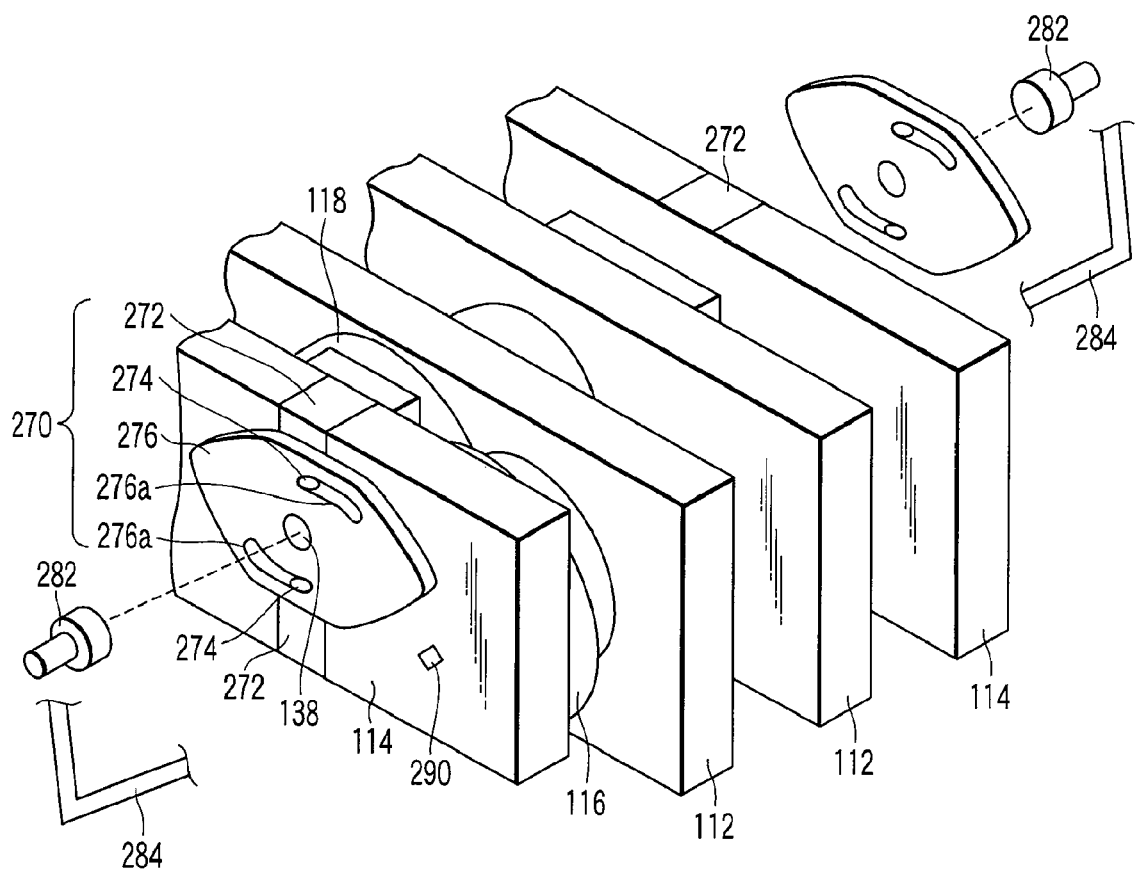
FIG. 8 is a schematic diagram showing the clutch mechanism disposed in the drive source unit of the base portion of the endoscope in the endoscopic system according to the second embodiment.

As shown in FIG. 6 to FIG. 9, the clutch mechanism 270 is disposed in the differential epicyclic gear mechanism 118c. The clutch mechanism 270 includes a pair of moving members (racks) 272, a pair of cam pins 274 and a rotation body 276. The moving members 272 is disposed slidably in a predetermined range over the second frame 114. That is, a recess is formed in the second frame 114 so that the moving members are slidably disposed therein. As shown in FIG. 7A and FIG. 7B, the moving members 272 include, at their opposite ends, engaging portions 272a which engage with the external teeth of the third gear 256. As shown in FIG. 6, the cam pins 274 are disposed in the moving members 272 from the second frame 114 to the outside. The rotation body 276 is rotatably disposed in the second frame 114. Further, as shown in FIG. 8, a pair of cam grooves 276a is formed in the rotation body 276. The cam pins 274 are disposed in the cam grooves 276a movably within the cam grooves 276a.

As shown in FIG. 6, the central axis of the rotation body 276 is coaxial with the above-mentioned sun gear shaft (second spur gear) 138. Further, the sun gear shaft 138 extends from the second frame 114 to the outside. The sun gear shaft 138 penetrates the rotation body 276. As shown in FIG. 8, a cap 282 fixed to the rotation body 276 is disposed at the end of the sun gear shaft 138. A clutch arm 284 is fixed to the cap 282. Thus, by the operation of the clutch arm 284, the rotation body 276 turns around the sun gear shaft 138 through the cap 282.

Figure 9:
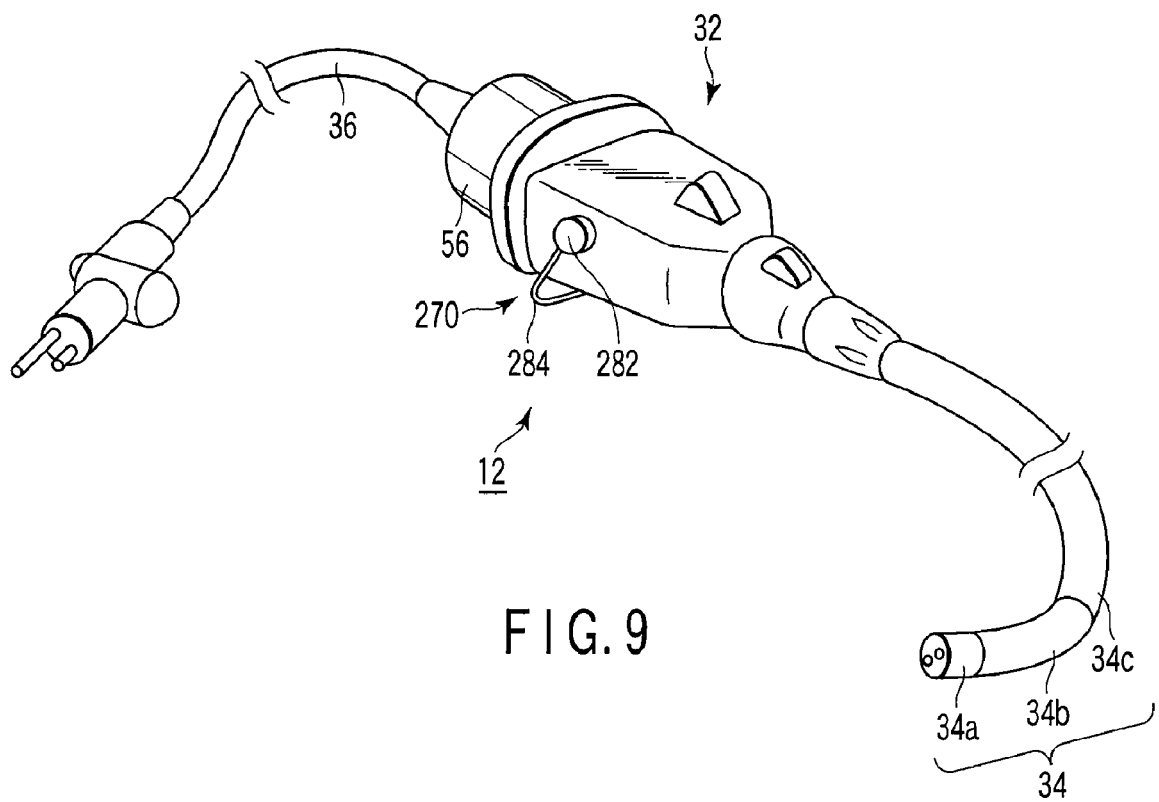
FIG. 9 is a schematic perspective view showing the endoscope in the endoscopic system according to the second embodiment wherein a clutch arm is disposed on the outside of the base portion.

In addition, as shown in FIG. 9, the clutch arm 284 couples a pair of drive source units 62 formed symmetrically with respect to the central axis of the insertion portion 34, outside a base portion 32. Thus, the clutch mechanism 270 of the pair of drive source units 62 is simultaneously switched by the operation of the clutch arm 284.

If the clutch arm 284 is operated in this manner, the cam grooves 276a also turn together with the rotation body 276 in accordance with the turning of the rotation body 276. Then, the cam pins 274 moves within the cam grooves 276a. Therefore, force is applied to the cam pins 274 from the cam grooves 276a, and the moving members 272 coupled to the cam pins 274 move while sliding over the second frame 114. That is, in accordance with the position of the clutch arm 284, the engaging portions 272a of the moving members 272 are switched between a position to gear (engage) with the external teeth of the third gear 256 and a position separated from the external teeth of the third gear 256.

In addition, as shown in FIG. 8, the rotation body 276 is not circularly formed, and is formed, for example, substantially elliptically. A microswitch 290 is fixed to the second frame 114 in the vicinity of the rotation body 276. The microswitch 290 detects the rotation of the rotation body 276. That is, the microswitch 290 detects the switching of the clutch arm 284. The microswitch 290 is electrically connected to a drive circuit 58. Thus, the state (position) of the clutch mechanism 270 is input to the drive circuit 58 from the microswitch 290. From the drive circuit 58, its signal is output to a system controller. In addition, the system controller may output such a signal to a remote controller 24. Moreover, the system controller may display the state of the clutch mechanism 270 on a monitor 26.

Next, the effects of the endoscope 12 according to this embodiment will be described.

First described are the effects in a state (first state) where the moving members 272 are moved by the operation of the clutch arm 284 to gear the engaging portions 272a of the moving members 272 with the external teeth of the third gear 256. At this point, the position of the rotation body 276 disposed in the second frame 114 is detected by the microswitch 290, and input to the system controller through the drive circuit 58. The system controller causes the monitor 26 to indicate this fact.

In this state, the operation unit of the remote controller 24 shown in FIG. 1 is operated. That is, the remote controller 24 is operated to bend a bending portion 34b of the endoscope 12. A signal output from the remote controller 24 is input to the drive circuit 58 of the base portion 32 through the system controller and a universal cable 36.

The drive circuit 58 rotates the drive shaft 116a of the motor 116 in a desired direction in accordance with the operation of the remote controller 24. Owing to the rotation of the drive shaft 116a of the motor 116, the second spur gear 134 rotates via the motor pinion 116b and the first spur gear 132. Thus, drive force is transmitted to the first gear (sun gear) 252 of the differential epicyclic gear mechanism 118c from the drive shaft 116a of the motor 116. Then, the first gear 252 rotates. Owing to the rotation of the first gear 252, the second gear (epicyclic gear) 254 geared with the first gear 252 rotates. At this point, as the external teeth of the third gear 256 are geared with and fixed to the engaging portions 272a of the moving members 272, the second gear 254 rotates on its axis and at the same time revolves around the first gear 252. That is, the second gear 254 moves along the inside (internal teeth) of the third gear 256 while rotating on its axis.

At this point, the fourth gear 258 is geared with the second gear 254 in the same manner as the third gear 256. The fourth gear 258 is pressed by the second gear 254 and slowly rotates so that the difference in the number of teeth between the fixed third gear 256 and the fourth gear 258 may be reduced. That is, the fourth gear 258 rotates around the central axis (the sun gear shaft 138) of the first gear 252. Thus, turning force is output from the output shaft 170 fixed to the fourth gear 258. Thus, the drive force of the drive shaft 116a of the motor 116 on the side of the second frame 114 is transferred to the output shaft 170 on the side of the first frame 112 such that the turning force is transmitted. At this point, turning force (axial force) is output from the output shaft 170 so that the rotation of the drive shaft 116a of the motor 116 is reduced to a great extent.

The fourth gear 258 outputs the turning force from the output shaft 170, and at the same time rotates the rotation shaft 120a of the potentiometer 120 via the meter gear 174 geared with the external teeth of the fourth gear 258. The potentiometer 120 detects the rotation number of the meter gear 174 having the same number of teeth as that of the external teeth of the fourth gear 258, and outputs the rotation number to the drive circuit 58. The drive circuit 58 judges the rotation amount of the meter gear 174 on the basis of the rotation number. That is, the drive circuit 58 judges the rotation amount of the fourth gear 258.

Thus, the output from the output shaft 170 is transmitted to the joint 82 of the drive force transmission unit 64 via the Oldham's coupling 180. Therefore, the drive force is transmitted to the angle wires 44 via sprockets 74 and chains 76. Consequently, the bending portion 34b is bended in a desired state.

Next described are the effects in a state (second state) where the moving members 272 are moved by the operation of the clutch arm 284 to separate the engaging portions 272a from the external teeth of the third gear 256.

In this state, the operation unit of the remote controller 24 shown in FIG. 1 is operated. That is, the remote controller 24 is operated to bend the bending portion 34b of the endoscope 12. A signal output from the remote controller 24 is input to the drive circuit 58 of the base portion 32 through the system controller and a universal cable 36.

The drive circuit 58 rotates the drive shaft 116a of the motor 116 in a desired direction in accordance with the operation of the remote controller 24. Owing to the rotation of the drive shaft 116a of the motor 116, the second spur gear 134 rotates via the motor pinion 116b and the first spur gear 132. Thus, drive force is transmitted to the first gear (sun gear) 252 from the drive shaft 116a of the motor 116. Then, the first gear 252 rotates. Owing to the rotation of the first gear 252, the second gear (epicyclic gear) 254 geared with the first gear 252 rotates on its axis. At this point, as the external teeth of the third gear 256 are away from the engaging portions 272a of the moving members 272, the second gear 254 rotates around the epicyclic gear shaft (second gear shaft) 264, and in some cases also revolves around the first gear 252. That is, the second gear 254 rotates on its axis at a fixed position, or in some cases rotates on its axis and also revolves around the first gear 252.

Then, the third gear 256 and the fourth gear 258 geared with the second gear 254 rotate. Thus, the output shaft 170 rotates. However, as the external teeth of the third gear 256 are not engaged with (fixed to) the engaging portions 272a of the moving members 272, the fourth gear 258 rotates, but torque is not generated. Therefore, turning force can not be output to the output shaft 170.

Thus, the turning force can not be transmitted from the output shaft 170 to the joint 82 of the drive force transmission unit 64 via the Oldham's coupling 180.

In addition, when the remote controller 24 is operated, the position of the rotation body 276 disposed in the second frame 114 is detected by the microswitch 290, and input to the system controller through the drive circuit 58. The system controller causes the monitor 26 to indicate this fact. Moreover, depending on the position of the clutch arm 284, the system controller can prevent a signal for the operation of bending the bending portion 34b from being output to the drive circuit 58 among signals input from the remote controller 24. Even if the system controller allows the drive circuit 58 to output the signal, the system controller can prevent the signal from being output from the drive circuit 58 to the motor 116.

Although the clutch mechanism 270 provided in the differential epicyclic gear mechanism 118c has been described here, it is also preferred to provide a similar clutch mechanism 270 in the epicyclic gear mechanism 118b of the endoscope 12 according to the first embodiment, for example, as shown in FIG. 3A and FIG. 3C.

As described above, the following effects can be obtained according to this embodiment.

The drive force of the drive shaft 116a of the motor 116 on the side of the second frame 114 is transferred to the opposite output shaft 170 on the side of the first frame 112 through the horizontal power transmission mechanism 118a and the differential epicyclic gear mechanism 118c such that the turning force is transmitted. Thus, the use of the differential epicyclic gear mechanism 118c makes it possible to provide a slower output from the output shaft 170 than that of the drive shaft 116a of the motor 116 in a desired reduction ratio.

Furthermore, the clutch mechanism 270 is provided in the differential epicyclic gear mechanism 118c, such that the third gear 256 is fixed when the drive force is to be transmitted to the bending portion 34b, and the third gear 256 is placed in a rotatable state when the drive force is not to be transmitted to the bending portion 34b. The switching between these states can be performed by simply operating the clutch arm 284. In particular, as the clutch arm 284 is coupled to the pair of drive source units 62, the clutch mechanism 270 of the pair of drive source units 62 can be switched to the same state by one operation. It is therefore possible to select, by one operation, whether to electrically actuate both the drive source unit 62 for vertically bending the bending portion 34b and the drive source unit 62 for horizontally bending the bending portion 34b. Moreover, the state of the clutch mechanism 270 can be easily checked by, for example, the monitor 26.

Figure 10:
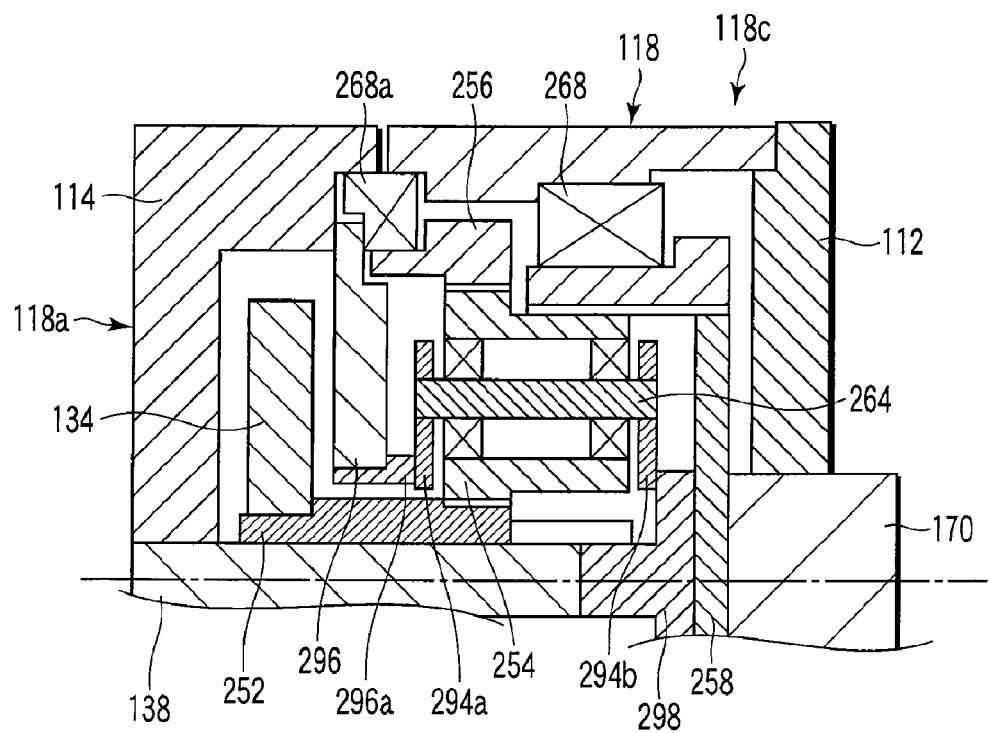
FIG. 10 is a schematic sectional view showing part of the drive source unit of the base portion of the endoscope in the endoscopic system according to the second embodiment.

FIG. 10 shows a modification of the differential epicyclic gear mechanism 118c according to the second embodiment.

As shown in FIG. 10, the epicyclic gear shaft 264 of the second gear 254 is disposed between first and second carriers 294a, 294b. The first carrier 294a is held by a first thrust receiver 296a provided in an inner flange 296. The third gear 256 and the inner flange 296 are supported by a bearing 268a. The second carrier 294b is held by a second thrust receiver 298 provided in the sun gear shaft 138. The second thrust receiver 298 is substantially T-shaped in section. The second thrust receiver 298 doubles as a thrust receiver for the fourth gear 258 and the output shaft 170.

Thus, as no bearings have to be provided for the first and second carriers 294a, 294b, the size of the differential epicyclic gear mechanism 118c can be reduced to the minimum.

While some of the embodiments have been specifically described above with reference to the drawings, this invention is not limited to the embodiments described above, and covers all the embodiments carried out without departing from the spirit thereof.

What is claimed is:

1. An endoscope comprising:
   an insertion portion including a bending portion;
   a base portion connected to the insertion portion;
   an operation wire extending from the bending portion toward the base portion;
   a drive source unit which is provided in the base portion and which is configured to drive the operation wire; and
   a drive force transmission unit which is connected to the operation wire and the drive source unit and which is configured to transmit drive force driven by the drive source unit to the operation wire,
   wherein the drive source unit includes:
   a first plane which is disposed inside the base portion and which is parallel to a central axis of the insertion portion;
   a second plane which is provided in parallel to the first plane and which is provided at a position farther from the central axis of the insertion portion than the first plane;
   a drive source which is provided to project from the first plane toward the second plane in a state supported by the first plane and which is configured to generate drive force in the second plane;
   a first gear as a sun gear which is connected to permit the transmission of the drive force of the drive source and which is rotatably held on the second plane;
   a second gear as an epicyclic gear which is geared with the first gear and which is configured to revolve around an outer periphery of the first gear;
   a third gear including internal teeth geared with the second gear, which is configured to hold the second gear revolvably around the first gear;
   a fourth gear which is rotated on the first plane in accordance with the revolving of the second gear and which is configured to axially drive the operation wire and configured to transmit the drive force from the drive source to the drive force transmission unit, wherein said fourth and said first gears having a common rotation axis; and
   a rotational position detection mechanism which is provided to project from the first plane toward the second plane in a state supported by the second plane and which is connected to the fourth gear to detect a rotational position of the fourth gear.

2. The endoscope according to claim 1, wherein the fourth gear includes internal teeth geared with the second gear, and the third gear and the fourth gear are different from each other in the number of teeth.

3. The endoscope according to claim 1, wherein the fourth gear includes internal teeth geared with the second gear and external teeth on its outer peripheral surface which transmits a rotation amount to the rotational position detection mechanism.

4. The endoscope according to claim 1, wherein the third gear further includes external teeth in addition to the internal teeth geared with the second gear, and
   the drive source unit is provided with a clutch mechanism which is configured to switch between a state engaged with the external teeth of the third gear to constrain its rotation and a state disengaged with the external teeth of the third gear to permit its rotation.

5. The endoscope according to claim 1, wherein the drive source unit includes:
   a first frame disposed in parallel to the first plane, having a first cutout in which part of the drive source provided to project from the first plane toward the second plane is disposed, and turnably holding the fourth gear; and
   a second frame which is disposed in parallel to the second plane and which is configured to turnably hold the first gear.

6. The endoscope according to claim 5, wherein the second frame includes a second cutout in which part of the rotational position detection mechanism is disposed.

7. The endoscope according to claim 5, wherein a spur gear which is configured to transmit the drive force from the drive source to the first gear is rotatably axially supported on the second frame.

8. The endoscope according to claim 1, further comprising:
   another operation wire extending from the bending portion toward the base portion: and
   another drive source unit which is provided in the base portion and which is configured to drive the another operation wire, and
   wherein the drive source unit and the another drive source unit are provided inside the base portion symmetrically with respect to the central axis of the insertion portion.

9. The endoscope according to claim 8, wherein the base portion includes a cylindrical member covering an outside thereof,
   the drive source is provided to project in a direction away from a central direction of the cylindrical member, and
   the rotational position detection mechanism is provided to project in a direction toward the central direction of the cylindrical member and opposite to the drive source.

* * * * *